United States Patent [19]

Woitun et al.

[11] 4,256,738
[45] Mar. 17, 1981

[54] 9-(ω-HETEROARYLAMINO-ALKYLAMINO)-ERYTHROMYCINS AND SALTS THEREOF

[75] Inventors: Eberhard Woitun; Bernd Wetzel; Roland Maier, all of Biberach an der Riss; Wolfgang Reuter, Laupertshausen; Uwe Lechner, Ummendorf; Rolf G. Werner; Hanns Goeth, both of Biberach an der Riss, all of Fed. Rep. of Germany

[73] Assignee: Boehringer Ingelheim GmbH, Ingelheim am Rhein, Fed. Rep. of Germany

[21] Appl. No.: 957,451

[22] Filed: Nov. 3, 1978

[30] Foreign Application Priority Data

Nov. 10, 1977 [DE] Fed. Rep. of Germany ....... 2750288

[51] Int. Cl.³ .................. A61K 31/70; C07H 17/09
[52] U.S. Cl. .......................... 424/180; 536/9; 536/17 R
[58] Field of Search .................. 536/9, 17; 424/180

[56] References Cited

U.S. PATENT DOCUMENTS

| | | | |
|---|---|---|---|
| 3,650,376 | 5/1972 | Massey | 536/9 |
| 3,794,635 | 2/1974 | Evans | 536/9 |
| 4,016,263 | 4/1977 | Wetzel et al. | 536/9 |

*Primary Examiner*—Johnnie R. Brown
*Assistant Examiner*—Blondel Hazel
*Attorney, Agent, or Firm*—Hammond & Littell, Weissenberger & Muserlian

[57] ABSTRACT

Compounds of the formula

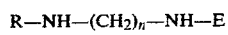

$$R-NH-(CH_2)_n-NH-E$$

wherein

R is a pyrimidinyl, a quinazolinyl, a 5,6,7,8-tetrahydroquinazolinyl, a thieno[3,2,-d]pyrimidinyl, a thieno[2,3-d]pyrimidyl, a pyrido[3,2-d]primidinyl, a 5,6-dihydro-4-pyrido[3,4-d]pyrimidinyl, an isothiazola[5,4-d]pyrimidinyl or a pyrimido[4,5-d]-pyrimidinyl group;

n is 2 or 3; and

E is the 9-erythromycyl group;

and non-toxic, pharmacologically acceptable acid addition salts thereof. The compounds as well as their salts are useful as antibacterials.

7 Claims, No Drawings

9-(ω-HETEROARYLAMINO-ALKYLAMINO)-ERYTHROMYCINS AND SALTS THEREOF

This invention relates to novel 9-(ω-heteroarylaminoalkylamino)-erythromycins and acid addition salts thereof, to a method of preparing these compounds, to pharmaceutical compositions containing them as active ingredients, and to methods of using them as antibacterials.

More particularly, the present invention relates to a novel class of erythromycin derivatives represented by the formula $$R-NH-(CH_2)_n-NH-E \quad (I)$$

wherein E is 9-erythromycyl of the formula [according to E. H. Massey et al; J. Med. Chem. 17, 105 (1974)].

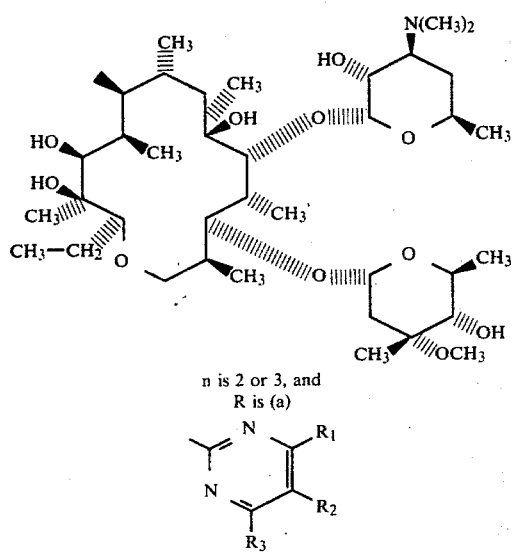

n is 2 or 3, and
R is (a)

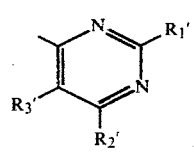

where
$R_1$ is hydrogen, methyl, hydroxyl, methoxy, amino, mono(alkyl of 1 to 4 carbon atoms)amino, di(alkyl of 1 to 4 carbon atoms)amino, mono (hydroxyalkyl of 1 to 4 carbon atoms)amino, di(hydroxyalkyl of 1 to 4 carbon atoms) amino, (alkoxyalkyl of 3 to 8 carbon atoms) amino, (phenoxy-alkyl of 1 to 3 carbon atoms) amino, (phenyl-alkyl of 1 to 3 carbon atoms) amino, di(phenyl-alkyl of 1 to 3 carbon atoms) amino or piperidino;
$R_2$ is hydrogen, phenyl, carbalkoxy of 2 to 4 carbon atoms or nitro; and
$R_3$ is hydrogen or methyl;

(b)

where
$R_1'$ is phenylamino; mono- or dichlorophenyl-amino; pyrrolidino; morpholino, thiomorpholino, piperazino or hexamethyleneimino, each of which may optionally be methyl- or benzyl-substituted; or has the meanings defined for $R_1$ above;
$R_2'$ is hydrogen, alkyl of 1 to 5 carbon atoms; phenyl, hydroxyl, methoxy or di(alkyl of 1 to 4 carbon atoms) amino; and
$R_3'$ is hydrogen; alkyl of 1 to 5 carbon atoms; benzyl, mono-, di- or trimethoxy-benzyl; phenyl; or carbalkoxy of 2 to 6 carbon atoms; or

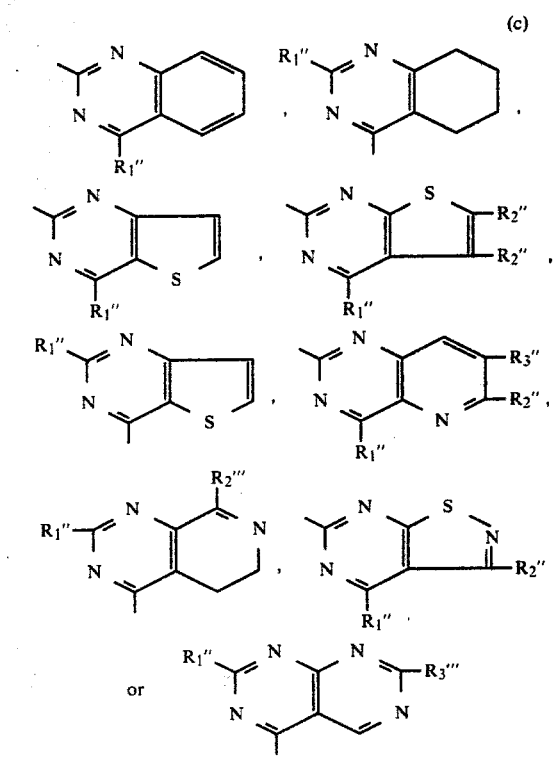

where
$R_1''$ is hydrogen, amino, mono(alkyl of 1 to 4 carbon atoms)amino, di(alkyl of 1 to 4 carbon atoms)amino or morpholino;
$R_2''$ is hydrogen or methyl;
$R_2'''$ is hydrogen or hydroxyl;
$R_3''$ is hydrogen or alkyl of 1 to 3 carbon atoms; and
$R_3'''$ is di(alkyl of 1 to 3 carbon atoms)amino or phenyl.

The compounds embraced by formula I may be prepared by reacting a 9-(aminoalkyl-amino)-erthromycin of the formula $$H_2N-(CH_2)_n-NH-E \quad (II)$$

wherein n and E have the same meanings as in formula I, with a compound of the formula $$R-Z \quad (III)$$

wherein R has the same meanings as in formula I, and Z is a leaving group, such as halogen, alkylsulfonyl, alkylsulfoxy or alkylmercapto, in a polar solvent at a temperature between 20° and 150° C. Examples of suitable polar solvents are alcohols, dimethylsulfoxide, acetonitrile, dioxane, 1-methyl-2-pyrrolidinone or hexamethylphosphoric acid triamide.

When Z is halogen, the reaction is preferably performed in the presence of a hydrogen halide-binding agent, for instance in the presence of an equimolar amount of an inorganic or organic base, such as sodium carbonate or triethylamine.

The aminoalkylamino-erythromycin starting compounds of the formula II where n is 3 may be prepared by reacting acrylonitrile with erythromycylamine [cf. R. Ryden et al., J. Med. Chem. 16, 1059–1060 (1973)], followed by reduction of the reaction product, 9-N-(2-cyanoethyl)-erythromycylamine, with hydrogen in the presence of a finely divided metallic catalyst, such as palladium, platinum, Raney nickel or Raney cobalt, in a solvent such as water, an alcohol or a cyclic ether.

For the preparation of a compound of the formula II where n is 2, nitroethylene is reacted with erythromycylamine under analogous conditions, and the reaction product, 9-N-(2-nitro-ethyl)-erthromycylamine, is thereafter reduced into the corresponding aminoalkylamino-erythromycin of the formula II in the same manner as described for 9-N-(2-cyanoethyl)-erythromycylamine in the preceding paragraph.

The starting compounds of the formula III are described in the literature or may be prepared in analogy to processes described in the literature.

Erythromycylamine may be prepared by catalytic hydrogenation of erythromycin-oxime [cf. E. H. Massey et al., J. Med. Chem. 17, 105–107 (1974)].

The end products of the formula I are organic bases and, therefore, form acid addition salts with inorganic or organic acids. Examples of non-toxic, pharmacologically acceptable acid addition salts are those formed with hydrochloric acid, hydrobromic acid, sulfuric acid, acetic acid, citric acid, laurylsulfonic acid, malic acid or the like.

The following examples illustrate the present invention and will enable others skilled in the art to understand it more completely. It should be understood, however, that the invention is not limited solely to the particular examples given below.

EXAMPLE 1

N-(3-[2-Dimethylamino-pyrimidin-4-yl-amino]-propyl)-erythromycylamine 5.8 gm (0.0073 mol) of N-(3-amino-propyl)-erythromycylamine, 1.18 gm (0.0075 mol) of 4-chloro-2-dimethylamino-pyrimidine and 0.7 gm (0.007 mol) of triethylamine were dissolved in 50 ml of absolute ethanol, and the solution was heated at 140° C. for 4 hours in a closed vessel. After cooling, the solvent was distilled off in vacuo, the solid residue was dissolved in methylene chloride, and the solution was extracted three times with water. The organic phase was dried over sodium sulfate, the solvent was distilled off in vacuo, and the solid residue was purified by column chromatography [adsorbant: aluminum oxide, basic; eluant: chloroform/methanol (60+0.8)]. After distilling off the eluant, a fine crystalline white substance was obtained.

Yield: 3.1 gm (47% of theory).

M.p. 101° C. (decomp.)

$C_{46}H_{84}N_6O_{12}$ (913.23): Calc.: C-60.50%; H-9.27%; N-9.20%; Found: C-60.20%; H-9.20%; N-9.40%.

The following compounds were prepared in analogous manner; for the sake of brevity, the starting compound N-(3-amino-propyl)-erythromycylamine is designated as A, and the starting compound N-(2-aminoethyl)-erythromycylamine is designated as B:

(a) N-(3-[2-(Methylamino-pyrimidin-4-yl-amino]-propyl)erythromycylamine by reaction of A with 4-chloro-2-methylamino-pyrimidine.

M.p. 117° C. (decomp.).

(b) N-(3-[2-Isopropylamino-pyrimidin-4-yl-amino]-propyl)erythromycylamine by reaction of A with 4-chloro-2-isopropylamino-pyrimidine.

M.p. 112° C. (decomp.).

(c) N-(3-Methoxyethylamino-pyrimidin-4-yl-amino]-propyl)erythromycylamine by reaction of A with 4-chloro-2-methoxyethylaminopyrimidine.

M.p. 110° C. (decomp.).

(d) N-(3-[2-Diethylamino-pyrimidin-4-yl-amino]propyl)erythroymycylamine by reaction of A with 4-chloro-2-diethylaminopyrimidine.

M.p. 99° C. (decomp.).

(e) N-(3-[2-Diethanolamino-pyrimidin-4-yl-amino]-propyl)erythromycylamine by reaction of A with 4-chloro-2-diethanolaminopyrimidine.

M.p. 108° C. (decomp.).

(f) N-(3-[2-benzylamino-pyrimidin-4-yl-amino]propyl)erythromycylamine by reaction of A with 2-benzylamino-4-chloropyrimidine.

M.p. 94° C. (decomp.).

(g) N-(3-[2-Morpholino-pyrimidin-4-yl-amino]propyl)erythromycylamine by reaction of A with 4-chloro-2-morpholino-pyrimidine.

M.p.: 116° C. (decomp.).

(h) N-(3-[2-Thiomorpholino-pyrimidin-4-yl-amino]-propyl)erythromycylamine by reaction of A with 4-chloro-2-thiomorpholinopyrimidine.

M.p. 121° C. (decomp.).

(i) N-(3-[2-Piperidino-pyrimidin-4-yl-amino]propyl)erythromycylamine by reaction of A with 4-chloro-2-piperidino-pyrimidine.

M.p. 113° C. (decomp.).

(k) N-(3-[2-(4-Benzyl)-piperidino-pyrimidin-4-yl-amino]propyl)-erythromycylamine by reaction of A with 4chloro-2-(4-benzyl)-piperidinopyrimidine.

M.p. 94° C. (decomp.).

(l) N-(3-[2-Ethanolamino-pyrimidin-4-yl-amino]propyl)erythromycylamine by reaction of A with 2-ethanolamino-4-chloropyrimidine M.p. 113° C. (decomp.).

(m) N-(3-[2-Dimethylamino-6-methyl-pyrimidin-4-yl-amino]propyl)-erythromycylamine by reaction of A with 4-chloro-2-dimethylamino-6-methylpyrimidine.

M.p. 109° C. (decomp.).

(n) N-(3-[6-Ethyl-2-dimethylamino-pyrimidin-4-yl-amino]propyl)-erythromycylamine by reaction of A with 6-ethyl-4-chloro-2-dimethylaminopyrimidine.

M.p. 91° C. (decomp.).

(o) N-(3-[2-Dimethylamino-6-isopropyl-pyrimidin-4-yl-amino]propyl)-erythromycylamine by reaction of A with 4-chloro-2-dimethylamino-6-isopropyl-pyrimidine.

M.p. 118° C. (decomp.).

(p) N-(3-[2-Dimethylamino-6-phenyl-pyrimidin-4-yl-amino]propyl)-erythromycylamine by reaction of A with 4-chloro-2-dimethylamino-6-phenylpyrimidine.
M.p. 123° C. (decomp.).

(q) N-(3-[2-Dimethylamino-6-hydroxy-pyrimidin-4-yl-amino]propyl)-erythromycylamine
by reaction of A with 4-chloro-2-dimethylamino-6-hydroxypyrimidine.
M.p. 175° C. (decomp.).

(r) N-(3-[2-Dimethylamino-5-methyl-pyrimidin-4-yl-amino]propyl)-erythromycylamine
by reaction of A with 4-chloro-2-dimethylamino-5-methylpyrimidine.
M.p. 114° C. (decomp.).

(s) N-(3-[5-Amyl-2-dimethylamino-pyrimidin-4-yl-amino]propyl)-erythromycylamine
by reaction of A with 5-amyl-4-chloro-2-dimethylaminopyrimidine.
M.p. 89° C. (decomp.).

(t) N-(3-[2-Dimethylamino-5-{3,4,5-trimethoxy-benzyl}pyrimidin-4-yl-amino]propyl)-erythromycylamine
by reaction of A with 4-chloro-2-dimethylamino-5-(3,4,5-trimethoxy-benzyl)-pyrimidine.
M.p. 97° C. (decomp.).

(u) N-(3-[2-Dimethylamino-5-phenyl-pyrimidin-4-yl-amino]propyl)-erythromycylamine
by reaction of A with 4-chloro-2-dimethylamino-5-phenyl pyrimidine.
M.p. 93° C. (decomp.).

(v) N-(3-[5-Carbethoxy-2-dimethylamino-pyrimidin-4-yl-amino]propyl)-erythromycylamine
by reaction of A with 5-carbethoxy-4-chloro-2-dimethylamino-pyrimidine.
M.p. 76° C. (decomp.).

(w) N-(3-[5-Benzyl-2-dimethylamino-6-methyl-pyrimidin-4-yl-amino]propyl)-erythromycylamine
by reaction of A with 5-benzyl-4-chloro-2-dimethylamino-6-methyl-pyrimidine.
M.p.: 105° C. (decomp.).

(x) N-(3-[5,6-Dimethyl-2-dimethylamino-pyrimidin-4-yl-amino]propyl)-erythromycylamine
by reaction of A with 4-chloro-5,6-dimethyl-2-dimethylamino-pyrimidine.
M.p. 103° C. (decomp.).

(y) N-(3-[5-Butyl-2-dimethylamino-6-methyl-pyrimidin-4-yl-amino]propyl)-erythromycylamine
by reaction of A with 5-butyl-4-chloro-2-dimethylamino-6-methyl-pyrimidine.
M.p. 89° C. (decomp.).

(z) N-(3-[6-Dimethylamino-pyrimidin-4-yl-amino]propyl)erythromycylamine
by reaction of A with 4-chloro-6-dimethylamino-pyrimidine.
M.p. 100° C. (decomp.).

(aa) N-(3-[6-Methoxy-pyrimidin-4-yl-amino]propyl)-erythromycylamine
by reaction of A with 4-chloro-6-methoxy-pyrimidine.
M.p. 84° C. (decomp.).

(ab) N-(3-[2-{4-Chloro-anilino}-6-methyl-pyrimidin-4-yl-amino]propyl)-erythromycylamine
by reaction of A with 2-(4-chloro)-anilino-4-chloro-6-methyl-pyrimidine.
M.p. 116° C. (decomp.).

(ac) N-(3-[2-Amino-6-methyl-pyrimidin-4-yl-amino]propyl)-erythromycylamine
by reaction of A with 2-amino-4-chloro-6-methyl-pyrimidine.
M.p. 121° C. (decomp.).

(ad) N-(3-[2-Amino-5-methyl-pyrimidin-4-yl-amino]propyl)-erythromycylamine
by reaction of A with 2-amino-4-chloro-5-methyl-pyrimidine.
M.p. 119° C. (decomp.).

(ae) N-(3-[2-Amino-5-{3,4,5-trimethoxy-benzyl}-pyrimidin-4-yl-amino]propyl)-erythromycylamine
by reaction of A with 2-amino-4-chloro-5-(3,4,5-trimethoxy)-benzyl-pyrimidine.
M.p. 104° C. (decomp.).

(af) N-(3-[4-Dimethylamino-pyrimidin-2-ylamino]propyl)-erythromycylamine
by reaction with A with 2-chloro-4-dimethylamino-pyrimidine.
M.p. 108° C. (decomp.).

(ag) N-(3-[4-Amino-pyrimidin-2-yl-amino]propyl)-erythromycylamine
by reaction of A with 4-amino-2-chloro-pyrimidine.
M.p. 116° C. (decomp.).

(ah) N-(3-[4-Isopropylamino-pyrimidin-2-yl-amino]propyl)-erythromycylamine
by reaction of A with 2-chloro-4-isopropylamino-pyrimidine.
M.p. 124° C. (decomp.).

(ak) N-(3-[4-Methoxyethylamino-pyrimidin-2-yl-amino]propyl)-erythromycylamine
by reaction of A with 2-chloro-4-methoxyethylamino-pyrimidine.
M.p. 107° C. (decomp.).

(ad) N-(3-[4-Benzylamino-pyrimidin-2-yl-amino]propyl)-erythromycylamine
by reaction of A with 2-chloro-4-benzylamino-pyrimidine.
M.p. 113° C. (decomp.).

(al) N-(3-[4-{2-Phenyl-ethylamino}-pyrimidin-2-yl-amino]propyl)-erythromycylamine
by reaction of A with 2-chloro-4-(2-phenyl-ethylamino)-pyrimidine
M.p. 94° C. (decomp.).

(am) N-(3-[4-{1-Phenyl-ethylamino}-pyrimidin-2-yl-amino]propyl)-erythromycylamine
by reaction of A with 2-chloro-4-(1-phenyl-ethylamino)-pyrimidine.
M.p. 97° C. (decomp.).

(an) N-(3-[4-{2-Phenoxy-ethylamino}-pyrimidin-2-yl-amino]propyl)-erythromycylamine
by reaction of A with 2-chloro-4-(2-phenoxy-ethylamino)-pyrimidine.
M.p. 73° C. (decomp.).

(ap) N-(3-[4-Piperidino-pyrimidin-2-yl-amino]propyl)-erythromycylamine
by reaction of A with 2-chloro-4-piperidino-pyrimidine.
M.p. 75° C. (decomp.).

(aq) N-(3-[4-Dibenzylamino-pyrimidin-2-yl-amino]propyl)-erythromycylamine
by reaction of A with 2-chloro-4-dibenzylamino-pyrimidine.
M.p. 87° C. (decomp.).

(ar) N-(3-[Pyrimidin-2-yl-amino]propyl)-erythromycylamine
by reaction of A with 2-chloro-pyrimidine.
M.p. 109° C. (decomp.).

(as) N-(3-[4-Methoxy-pyrimidin-2-yl-amino]propyl)-erythromycylamine
by reaction of A with 2-chloro-4-methoxy-pyrimidine.

M.p. 99° C. (decomp.).
(at) N-(3-[4-Dimethylamino-6-methyl-pyrimidin-2-yl-amino]propyl)-erythromycylamine
by reaction of A with 2-chloro-4-dimethylamino-6-methyl-pyrimidine.
M.p. 116° C. (decomp.).
(au) N-(3-[4-Amino-5-carbethoxy-pyrimidin-2-yl-amino]propyl)-erythromycylamine
by reaction of A with 4-amino-5-carbethoxy-2-chloro-pyrimidine.
M.p 141° C. (decomp.).
(av) N-(3-[5-Carbethoxy-4-hydroxy-pyrimidin-2-yl-amino]propyl)-erythromycylamine
by reaction of A with 2-chloro-5-carbethoxy-4-hydroxy-pyrimidine.
M.p. 110° C. (decomp.).
(aw) N-(3-[6-methyl-5-nitro-4-piperidino-pyrimidin-2-yl-amino]propyl)-erythromycylamine
by reaction of A with 2-chloro-6-methyl-5-nitro-4-piperidino-pyrimidine.
M.p. 112° C. (decomp.).
(ax) N-(3-[4,6-Dimethyl-5-phenyl-pyrimidin-2-yl-amino]propyl)-erythromycylamine
by reaction of A with 2-chloro-4,6-dimethyl-5-phenyl-pyrimidine.
M.p. 108° C. (decomp.).
(ay) N-(2-[4-Dimethylamino-pyrimidin-2-yl-amino]ethyl)-erythromycylamine
by reaction of B with 2-chloro-4-dimethylamino-pyrimidine.
M.p. 103° C. (decomp.).
(az) N-(3-[2-(Dimethylamino-5,6,7,8-tetrahydro-quinazolin-4-yl-amino]propyl)-erythromycylamine
by reaction of A with 2-dimethylamino-4-chloro-5,6,7,8-tetrahydro-quinazoline.
M.p. 116° C. (decomp.).
(ba) N-(3-[4-Dimethylamino-quinazolin-2-yl-amino]-propyl)-erythromycylamine
by reaction of A with 2-chloro-4-dimethylamino-quinazoline.
M.p. 102° C. (decomp.).
(bc) N-(3-[4-Dimethylamino-thieno[3,2-d]pyrimidin-2-yl-amino]propyl)-erythromycylamine
by reaction of A with 2-chloro-4-dimethylamino-thieno[3,2-d]pyrimidine.
M.p. 120° C. (decomp.).
(bd) N-(3-[4-Propylamino-thieno[3,2-d]pyrimidin-2-yl-amino]propyl)-erythromycylamine
by reaction of A with 2-chloro-4-propylamino-thieno[3,2-d]pyrimidine.
M.p. 127° C. (decomp.).
(be) N-(3-[4-Morpholino-thieno[3,2-d]pyrimidin-2-yl-amino]propyl-erythromycylamine
by reaction of A with 2-chloro-4-morpholino-thieno[3,2-d]pyrimidine
M.p. 116° C. (decomp.).
(bf) N-(3-[Thieno[2,3-d]pyrimidin-4-yl-amino]propyl)-erythromycylamine
by reaction of A with 4-chloro-thieno[2,3-d]pyrimidine.
M.p. 110° C. (decomp.).
(bg) N-(3-[2-Morpholino-thieno[2,3-d]pyrimidin-4-yl-amino]propyl)-erythromycylamine
by reaction of A with 4-chloro-2-morpholino-thieno[2,3-d]pyrimidine.
M.p. 119° C. (decomp.).
(bi) N-(3-[4-Dimethylamino-5,6-dimethyl-thieno[2,3-d]pyrimidin-2-ylamino]propyl)-erythromycylamine
by reaction of A with 2-chloro-4-dimethylamino-5,6-dimethyl-thieno[2,3-d]pyrimidine.
M.p. 113° C. (decomp.).
(bk) N-(3-[4-Dimethylamino-5,6-tetramethylene-thieno[2,3-d]pyrimidin-2-yl-amino]propyl)-erythromycylamine
by reaction of A with 2-chloro-4-dimethylamino-5,6-tetramethylene-thieno[2,3-d]pyrimidine.
M.p. 124° C. (decomp.).
(bl) N-(3-[5-Methyl-4-morpholino-isothiazolo[5,4-d]pyrimidin-2-yl-amino]propyl)-erythromycylamine
by reaction of A with 2-chloro-5-methyl-4-morpholino-isothiazolo[5,4-d]pyrimidine.
M.p. 125° C. (decomp.).
(bm) N-(3-[4-Dimethylamino-pyrido[3,2-d]pyrimidin-2-yl-amino]propyl)-erythromycylamine
by reaction of A with 2-chloro-4-dimethylamino-pyrido[3,2-d]pyrimidine.
M.p. 109° C. (decomp.).
(bn) N-(3-[4-Amino-6-methyl-pyrido[3,2-d]pyrimidin-2-yl-amino]-propyl)-erythromycylamine
by reaction of A with 4-amino-2-chloro-6-methyl-pyrido[3,2-d]pyrimidine.
M.p. 88° C. (decomp.).
(bo) N-(3-[4-Dimethylamino-7-methyl-pyrido[3,2-d]pyrimidin-2-yl-amino]propyl)-erythromycylamine
by reaction of A with 2-chloro-4-dimethylamino-7-methyl-pyrido[3,2-d]pyrimidine.
M.p. 104° C. (decomp.).
(bp) N-(3-[2-Dimethylamino-8-hydroxy-5,6-dihydro-pyrido[3,4-d]pyrimidin-4-yl-amino]propyl)-erythromycylamine
by reaction of A with 4-chloro-2-dimethylamino-8-hydroxy-5,6-dihydro-pyrido[3,4-d]pyrimidine.
M.p. 115° C. (decomp.).
(bq) N-(3-[2,7-Bis-dimethylamino-pyrimido[4,5-d]pyrimidin-4-yl-amino]-propyl)-erythromycylamine
by reaction of A with 2,7-bis-dimethylamino-4-chloro-pyrimido[4,5-d]pyrimidine.
M.p. 159° C. (decomp.).
(br) N-(3-[2-Morpholino-7-phenyl-pyrimido[4,5-d]pyrimidin-4-yl-amino]propyl)-erythromycylamine
by reaction of A with 4-chloro-2-morpholino-7-phenyl-pyrimido[4,5-d]pyrimidine.
M.p. 172° C. (decomp.).

EXAMPLE 2

N-(3-[2-Dimethylamino-6-methyl-pyrimidine-4-yl-amino]propyl)-erythromycylamine 7.92 gm (0.01 mol) of N-(3-amino-propyl)-erythromycylamine and 2.15 gm (0.01 mol) of 2-dimethylamino-6-methyl-4-methyl-sulfonyl-pyrimidine were dissolved in 50 ml of dimethylsulfoxide, and the solution was heated for 5 hours at 100° C. After cooling the solvent was distilled off in a high vacuum, the residue was dissolved in methylene chloride and the solution was extracted with water. The organic phase was dried over sodium sulfate, the solvent was removed, and the residue was purified by column-chromatography [adsorbant: aluminum oxide, basic eluant: chloroform/methanol (30+0.5)].

The desired compound was obtained as a white, crystalline powder.
Yield: 4.7 gm (51% of theory).
M.p. 109° C. (decomp.).
$C_{47}H_{86}N_6O_{12}$ (927.25); Calc.: C-60.88%, H-9.35%; N-9.06%; Found: C-60.90%; H-9.38%; N-9.01%.

The compounds of the present invention, that is, those embraced by formula I above and their non-toxic, pharmacologically acceptable acid addition salts, have useful pharmacodynamic properties. More particularly, they exhibit very effective antibacterial properties in vitro as well as in warm-blooded animals such as mice, especially against gram-positive and gram-negative bacteria, for instance against Staphylococcus aureus SG 511 and Streptococus aronson at concentrations of 0.3 to 5.0 mgm/ml, and against Escherichia coli at concentrations of 5 to 40 mgm/ml.

The antibacterial properties of the compounds of this invention were ascertained by the agar diffusion test and the series dilution test in analogy to the method described by P. Klein in "Bakteriologische Grundlagen der chemotherapeutischen Laboratoriumspraxis", Springer-Verlag, 1957, pages 53–76 and 87–109.

The following compounds are particularly effective antibacterials:

N-(3-[2-dimethylamino-pyrimidin-4-yl-amino]propyl)-erythromycylamine,
N-(3-[2-dimethylamino-5-methyl-pyrimidin-4-yl-amino]propyl)-erythromycylamine,
N-(3-[2-dimethylamino-6-methyl-pyrimidin-4-yl-amino]propyl)-erythromycylamine,
N-(3-[6-dimethylamino-pyrimidin-4-yl-amino]propyl)-erythromycylamine,
N-(3-[2-dimethylamino-6-ethyl-pyrimidin-4-yl-amino]propyl)-erythromycylamine,
N-(3-[2-dimethylamino-5,6,7,8-tetrahydroquinazolin-4-yl-amino]propyl)-erythromycylamine,
N-(3-[4-dimethylamino-pyrimidin-2-yl-amino]propyl)-erythromycylamine,
N-(3-[4-phenethylamino-pyrimidin-2-yl-amino]propyl)-erythromycylamine,
N-(3-[2-dimethylamino-5-phenyl-pyrimidin-4-yl-amino]-propyl)-erythromycylamine,
N-(3-[2-amino-5-methyl-pyrimidin-4-yl-amino]-propyl)-erythromycylamine,
N-(3-[4-dimethylamino-quinazolin-2-yl-amino]propyl)-erythromycylamine,
N-(3-[4-dimethylamino-thieno[3,2-d]pyrimidin-2-yl-amino]propyl)-erythromycylamine, and
N-(3-[4-phenoxyethylamino-pyrimidin-2-yl-amino]-propyl)-erythromycylamine.

The median lethal dose (LD$_{50}$), as determined in mice after peroral and subcutaneous administration, was higher than 1.5 gm/kg for all compounds.

For pharmaceutical purposes the compounds of the present invention are administered to warm-blooded animals perorally or parenterally, preferably perorally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. One effective oral dosage unit of the compounds according to the present invention is from 0.83 to 8.4 mgm/kg body weight, preferably 1.67 to 4.17 mgm/kg body weight. The daily dose rate is 0.0083 to 0.067 gm/kg, preferably 0.016 to 0.033 gm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

Tablets

The tablet composition is compounded from the following ingredients:

| | |
|---|---|
| N-(3-[2-Dimethylamino-pyrimidin-4-yl-amino]-propyl)-erythromycylamine | 100.0 parts |
| Lactose | 63.0 parts |
| Potato starch | 50.0 parts |
| Polyvinylpyrrolidone | 5.0 parts |
| Magnesium stearate | 2.0 parts |
| Total | 220.0 parts |

Preparation:

The above ingredient, the lactose and the potatoe starch are intimately admixed with each other, the mixture is moistened with an aqueous 10% solution of the polyvinylpyrrolidone, the moist mass is granulated by passing it through a 1.5 mm-mesh screen and the granulate is dried at 45° C. and again passed through the screen. The dry granulate is admixed with the magnesium stearate, and the composition is compressed into 220 mgm-tablets in a conventional tablet making machine. Each tablet is an oral dosage unit composition containing 100 mgm of the active ingredient.

EXAMPLE 4

Coated pills

The pill core composition is compounded from the following ingredients:

| | |
|---|---|
| N-(3-[2-Dimethylamino-pyrimidin-4-yl-amino]-propyl)-erythromycylamine | 100.0 parts |
| Lactose | 30.0 parts |
| Corn Starch | 30.0 parts |
| Gelatin | 3.0 parts |
| Cellulose, microcrystalline | 6.0 parts |
| Magnesium stearate | 1.0 parts |
| Total | 170.0 parts |

Preparation:

The active ingredient, the lactose and the corn starch are intimately admixed with each other, the mixture is moistened with an aqueous 12% solution of the gelatin, the moist mass is granulated by passing it through a 1.5 mm-mesh screen, and the granulate is dried at 45° C. and again passed through a 1.0 mm-mesh screen. The dry granulate is admixed with the cellulose and the magnesium stearate, and the composition is compressed into 170 mgm-pill cores which are then coated with a thin shell consisting essentially of sugar and talcum and finally polished with beeswax. Each coated pill is an oral dosage unit composition containing 100 mgm of the active ingredient.

Any one of the other compounds embraced by formula I or a non-toxic, pharmacologically acceptable acid addition salt thereof may be substituted for the particular active ingredient in Examples 3 and 4. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound selected from the group consisting of N-[3-(2-dimethylamino-pyrimidin-4-yl-amino)-propyl]-erythromycylamine, N-[3-(2-dimethylamino-5-methyl-pyrimidin-4-yl-amino-propyl]-erythromycylamine, N-[3-(2-dimethylamino-5,6,7,8-tetrahydroquinazolin-4-yl-amino)-propyl]-erythromycylamine, N-[3-(6-dimethylamino-pyrimidin-4-yl-amino)-propyl]-erythromycylamine, and non-toxic, pharmacologically acceptable acid addition salts thereof.

2. A compound of claim 1, which is N-[3-(2-dimethylamino-5-methyl-pyrimidin-4-yl-amino)-propyl]-erythromycylamine or a non-toxic, pharmacologically acceptable acid salt thereof.

3. A compound of claim 1, which is N-[3-(2-dimethylamino-5,6,7,8-tetrahydro-quinazolin-4-yl-amino)-propyl]-erythromycylamine or a non-toxic, pharmacologically acceptable acid salt thereof.

4. A compound of claim 1, which is N-[3-(6-dimethylamino-pyrimidin-4-yl-)-propyl]-erythromycylamine or a non-toxic, pharmacologically acceptable acid salt thereof.

5. A compound of claim 1, which is N-[3-(2-dimethylamino-pyrimidin-4-yl-amino)-propyl]-erythromycylamine or a non-toxic, pharmacologically acceptable acid salt thereof.

6. An antibacterial pharmaceutical dosage unit composition consisting essentially of an inert pharmaceutical carrier and an effective antibacterial amount of a compound of claim 1.

7. The method of destroying or suppressing the growth or reproduction of bacteria in a warm-blooded animal, which comprises perorally or parenterally administering to said animal an effective antibacterial amount of a compound of claim 1.

* * * * *

UNITED STATES PATENT AND TRADEMARK OFFICE
CERTIFICATE OF CORRECTION

PATENT NO. : 4,256,738

DATED : March 17, 1981

INVENTOR(S) : EBERHARD WOITUN ET AL.

It is certified that error appears in the above—identified patent and that said Letters Patent is hereby corrected as shown below:

Column 1, first structural formula: The portion of the formula which reads

" 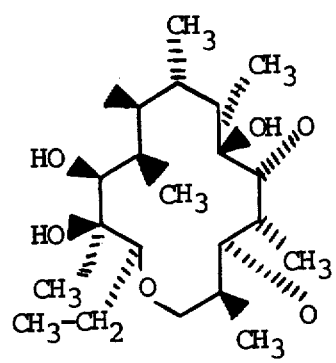 "

should read

-- 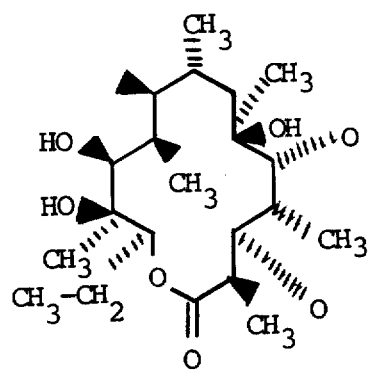 --

UNITED STATES PATENT AND TRADEMARK OFFICE
CERTIFICATE OF CORRECTION

PATENT NO. : 4,256,738

DATED : March 17, 1981

INVENTOR(S) : EBERHARD WOITUN ET AL.

It is certified that error appears in the above—identified patent and that said Letters Patent is hereby corrected as shown below:

Column 4, lines 12, 22, 27 and 47: "amino]propyl-" should read -- amino]propyl)- --.

lines 13, 23, 28 and 48: Delete ")".

line 44: "4chloro" should read -- 4-chloro --.

Column 6, line 26: "(ak)" should read -- (ai) --.

line 31: "(ad)" should read -- (ak) --.

Signed and Sealed this

Thirtieth Day of June 1981

[SEAL]

Attest:

RENE D. TEGTMEYER

Attesting Officer

Acting Commissioner of Patents and Trademarks